| (12) | United States Patent | (10) Patent No.: | US 8,925,386 B2 |
|---|---|---|---|
| | Oshiki | (45) Date of Patent: | Jan. 6, 2015 |

(54) ULTRASONIC DIAGNOSTIC APPARATUS

(75) Inventor: Mitsuhiro Oshiki, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 890 days.

(21) Appl. No.: 13/126,347

(22) PCT Filed: Oct. 21, 2009

(86) PCT No.: PCT/JP2009/068092
§ 371 (c)(1),
(2), (4) Date: Apr. 27, 2011

(87) PCT Pub. No.: WO2010/053008
PCT Pub. Date: May 14, 2010

(65) Prior Publication Data
US 2011/0203374 A1    Aug. 25, 2011

(30) Foreign Application Priority Data

Nov. 6, 2008  (JP) .................................. 2008-285573

(51) Int. Cl.
*B06B 1/02* (2006.01)
*A61B 8/00* (2006.01)
*G01S 7/52* (2006.01)

(52) U.S. Cl.
CPC ................ *B06B 1/0223* (2013.01); *A61B 8/56* (2013.01); *G01S 7/52084* (2013.01); *G01S 7/52096* (2013.01); *G01S 7/5202* (2013.01); *A61B 2560/0209* (2013.01)
USPC ................................. 73/602; 73/626; 73/628

(58) Field of Classification Search
USPC ..................... 73/602, 625, 626, 628
See application file for complete search history.

(56) References Cited

U.S. PATENT DOCUMENTS

| 6,511,429 B1* | 1/2003 | Fatemi et al. | 600/443 |
|---|---|---|---|
| 2004/0174203 A1* | 9/2004 | Wodnicki | 327/427 |
| 2007/0016026 A1* | 1/2007 | Thomenius et al. | 600/437 |
| 2010/0004539 A1* | 1/2010 | Chen et al. | 600/445 |

FOREIGN PATENT DOCUMENTS

| JP | 05-056973 | | 3/1993 |
|---|---|---|---|
| JP | 2001268694 | | 9/2001 |
| JP | 2001268694 A | * | 9/2001 |
| JP | 2001-269336 | | 10/2001 |
| JP | 2002-065672 | | 3/2002 |
| JP | 2003-175035 | | 6/2003 |
| JP | 2003-235842 | | 8/2003 |
| JP | 2004-073883 | | 3/2004 |
| JP | 2005-152450 | | 6/2005 |
| JP | 2005-192868 | | 7/2005 |
| JP | 2006-000287 | | 1/2006 |
| JP | 2006-101997 | | 4/2006 |
| JP | 2006-122449 | | 5/2006 |
| JP | 2006-217942 | | 8/2006 |

* cited by examiner

*Primary Examiner* — Peter Macchiarolo
*Assistant Examiner* — Rose M Miller
(74) *Attorney, Agent, or Firm* — Brundidge & Stanger, P.C.

(57) ABSTRACT

An ultrasonic diagnostic apparatus having an ultrasonic probe configured to transmit and receive an ultrasonic wave, a transmitter for configured to supply a signal to the ultrasonic probe and forming an ultrasonic beam, a receiver configured to receive a reception signal obtained by transmitting the ultrasonic beam to an object, a signal processor configured to form an ultrasonic image on the basis of the reception signal, a display unit configured to display the ultrasonic image, and a control unit configured to control the transmitter, the receiver, the signal processor and the display unit, comprising a setting unit configured to set an operation mode of the transmitter to a low power consumption operation mode or a high spatial resolution operation mode.

5 Claims, 8 Drawing Sheets

ULTRASONIC DIAGNOSTIC APPARATUS

TECHNICAL FIELD

The present invention relates to an ultrasonic diagnostic apparatus, and particularly to an ultrasonic transducer driving technique which can select the priority of suppression of power consumption and spatial resolution of a diagnostic image.

BACKGROUND ART

According to an ultrasonic diagnostic apparatus, a voltage is applied to a transducer which is mainly constructed by a piezoelectric material, an ultrasonic wave generated from the transducer is transmitted to an object, and various information is taken out from a reflection wave of the ultrasonic wave, thereby obtaining information of the inside of the object.

Ultrasonic image quality is dependent on how excellently ultrasonic wave transmission/reception beams can be formed over all depths. The wave reception beam has higher precision by digital phasing and can implement dynamic focus. On the other hand, the wave transmission beam must sacrifice a frame rate thereof in order to implement dynamic focus, and thus it is required to form an excellent beam having high spatial resolution in one beam formation. That is, it is required to lengthen a focal depth and suppress a side lobe. Therefore, it is indispensable to weight a time direction of a waveform of a transmission wave and an aperture direction used for beam formation.

Formation of an amplitude-weighted waveform which is effective to suppress the side lobe, enhance a contrast spatial resolution, etc. by a digital phasing technique has been recently facilitated even in wave-transmission phasing.

A linear wave-transmission amplifying circuit for precisely amplifying any transmission signal of minute amplitude output from a DA converter to a high voltage is generally necessary to drive a transducer by using the weighted waveform described above and generate an ultrasonic wave. A transducer disposed in a probe has an action of converting an electrical signal to an ultrasonic signal. In order to form an ultrasonic beam and obtain sufficient information for diagnosis, it is necessary to apply a signal of about one hundred and several tens volts and thus it is necessary to amplify the output from the DA converter until this level.

In general, in the ultrasonic diagnostic apparatus, the linear wave-transmission amplifying circuit is frequently implemented by a P-channel (hereinafter referred to as Pch) and an N channel (hereinafter referred to as Nch) of a field effect transistor (Field Effect Transistor: FET) or a transistor which enables flow of current whose amount is necessary to drive a probe having a relatively low impedance or by joining NPN and PNP types using these transistors. In order to simplify the description, the description will be described by specializing FET, however, the same effect can be obtained by electrical elements having a current amplifying action such as a transistor, etc.

With respect to FET, various circuit parameters such as capacity, ON-resistance under operation, etc. are different between the Pch and the Nch. Therefore, in order to compensate for this as much as possible and implement a linear amplifying operation irrespective of the magnitude of an input signal, it is necessary to make bias current of about several mA flow steadily even when no signal is input.

Furthermore, as described above, a maximum applied voltage of about hundred and several tens volts is required to drive the probe as described above, and thus for example, about ±100V is required to a power supply at a device side. The bias current described above is required per channel, and it is consumed in the power supply of about ±100V. Therefore, heat generation of several W to several tens W occurs necessarily as the whole of the ultrasonic diagnostic apparatus.

As described above, in order to enhance the spatial resolution of diagnostic images, a wave-transmission circuit which can perform the linear amplification operation is required, and large power consumption is required as the whole device to implement this circuit system.

Plural attempts to reduce this large power consumption have been proposed. According to Patent Document 1, an ultrasonic diagnostic apparatus is provided with means for determining, as power save units, operation-unnecessary units and operation-limitable units out of plural units constituting the device in accordance with an operation condition of the device when a diagnostic image is formed, and the operation of each unit is limited at a proper timing to suppress power consumption.

Furthermore, according to Patent Document 2, a power supply voltage value to be supplied to a transmission circuit is switched to another fixed voltage source or another control voltage source in accordance with a transmission voltage supplied to an ultrasonic probe in the transmission circuit, whereby the power consumption in the transmission circuit and the heat generation caused by the power consumption are reduced.

PRIOR ART DOCUMENT

Patent Document

Patent Document 1: JP-A-2003-175035
Patent Document 2: JP-A-2006-101997

SUMMARY OF THE INVENTION

Problem to be Solved by the Invention

The Patent Document 1 takes a countermeasure based on turn-on or switching of a power supply on a circuit-module basis dependently on transmission/reception or an operation mode or based on suppression of power consumption, and performs timing-dependent control when the power consumption of the ultrasonic diagnostic apparatus is reduced. Specifically, power supply to a transmission module which is not required to operate at a reception timing is stopped during reception period, for example.

Furthermore, the Patent Document 2 performs circuit using power supply control dependent on an operation mode. For example, this is particularly effective to two wave transmission systems having different characteristics based on a pulse Doppler mode in which several waves called as burst wave and having relatively large amplitude are transmitted at a fixed interval, and a continuous wave Doppler mode in which continuous waves of relatively small amplitude are transmitted. By selecting the power supply in accordance with this required amplitude amount, the heat generation in a transmission circuit unit can be limited.

It has been proposed in the prior arts to perform the suppression of power consumption at the operation timing represented by transmission, reception, etc. and the suppression of power consumption dependent on the diagnosis mode represented by the pulse Dopper and the continuous wave Doppler. However, there is not any proposal paying attention to the relationship between phasing precision and power consumption.

As described above, the linear wave-transmission amplifying circuit is indispensable to achieve high spatial resolution, and it is also apparent that more power is consumed to implement the high spatial resolution. However, in such a case that a larger amount of diagnosis is required to be performed even at some sacrifice of the spatial resolution at an outdoor screening place where a battery-based operation is necessary, it cannot be implemented by the prior arts.

An object of the present invention is to provide an ultrasonic diagnostic apparatus which can select high resolution or, low power consumption.

Means of Solving the Problem

In order to attain the above object, according to the present invention, in an ultrasonic diagnostic apparatus having an ultrasonic probe configured to transmit and receive an ultrasonic wave, a transmitter configured to supply a signal to the ultrasonic probe and form an ultrasonic beam, a receiver configured to receive a reception signal obtained by transmitting the ultrasonic beam to an object, a signal processor configured to form an ultrasonic image on the basis of the reception signal, a display unit configured to display the ultrasonic image, and a control unit configured to control the transmitter, the receiver, the signal processor and the display unit, the transmitter has a wave-transmission circuit that can select a low power consumption operation mode and a high spatial resolution operation mode.

Furthermore, in the present invention, an input device unit for selecting the low power consumption operation mode and the high spatial resolution operation mode is disposed on the display unit or at the probe.

Still furthermore, in the present invention, the input device unit can select modes of plural stages between the low power consumption operation mode and the high spatial resolution operation mode.

That is, in order to attain the above object, the ultrasonic diagnostic apparatus of the present invention accompanies stationary power consumption with respect to the wave-transmission circuit for driving a transducer when higher spatial resolution is required. However, it enables the wave-transmission circuit to operate as a linear wave-transmission amplifying circuit for enabling flow of bias current which can be subjected to arbitrary waveform amplification. On the other hand, when more clinical examinations are required to be executed although the spatial resolution is lowered in some degree, the bias current consumed in the above linear waveform amplifying circuit is reduced or stopped, so that a linear amplification operation as the wave-transmission circuit is restricted in linear operation range or lost, however, the power consumption is reduced.

For example, according to an ultrasonic diagnostic apparatus operated with a battery, the power consumption can be reduced and further an operating lifetime as a device can be extended with sacrificing a phasing precision.

For the enhancement of the spatial resolution based on waveform weighting, the transmission circuit which can perform the linear amplification operation is described above, however, the present invention is not limited to this transmission circuit. For example, the same effect can be achieved by a transmission circuit using plural power supplies which have some stages for amplitude weighting and can transmit equal waveforms in a pseudo style.

Effect of the Invention

According to the present invention, there can be provided an ultrasonic diagnostic apparatus in which the priority of the suppression of the power consumption and the enhancement of the spatial resolution can be stepwise selected through an external input device by a user of the device. Preferably, the stepwise selection of the priority corresponds to a selection of a wave-transmission type, that is, a control of a bias current in a transmission circuit of the ultrasonic diagnostic apparatus. As a result, an optimum device using environment which is matched with an operation condition can be provided.

According to the construction of the present invention described above, there can be provided an ultrasonic diagnostic apparatus in which the device user can arbitrarily select the priority of the reduction of the power consumption and the enhancement of the spatial resolution by the external input device.

MODES FOR CARRYING OUT THE INVENTION

Embodiments of the present invention will be described hereunder according to drawings, however, the basic of this invention will be first described.

Figure 1:
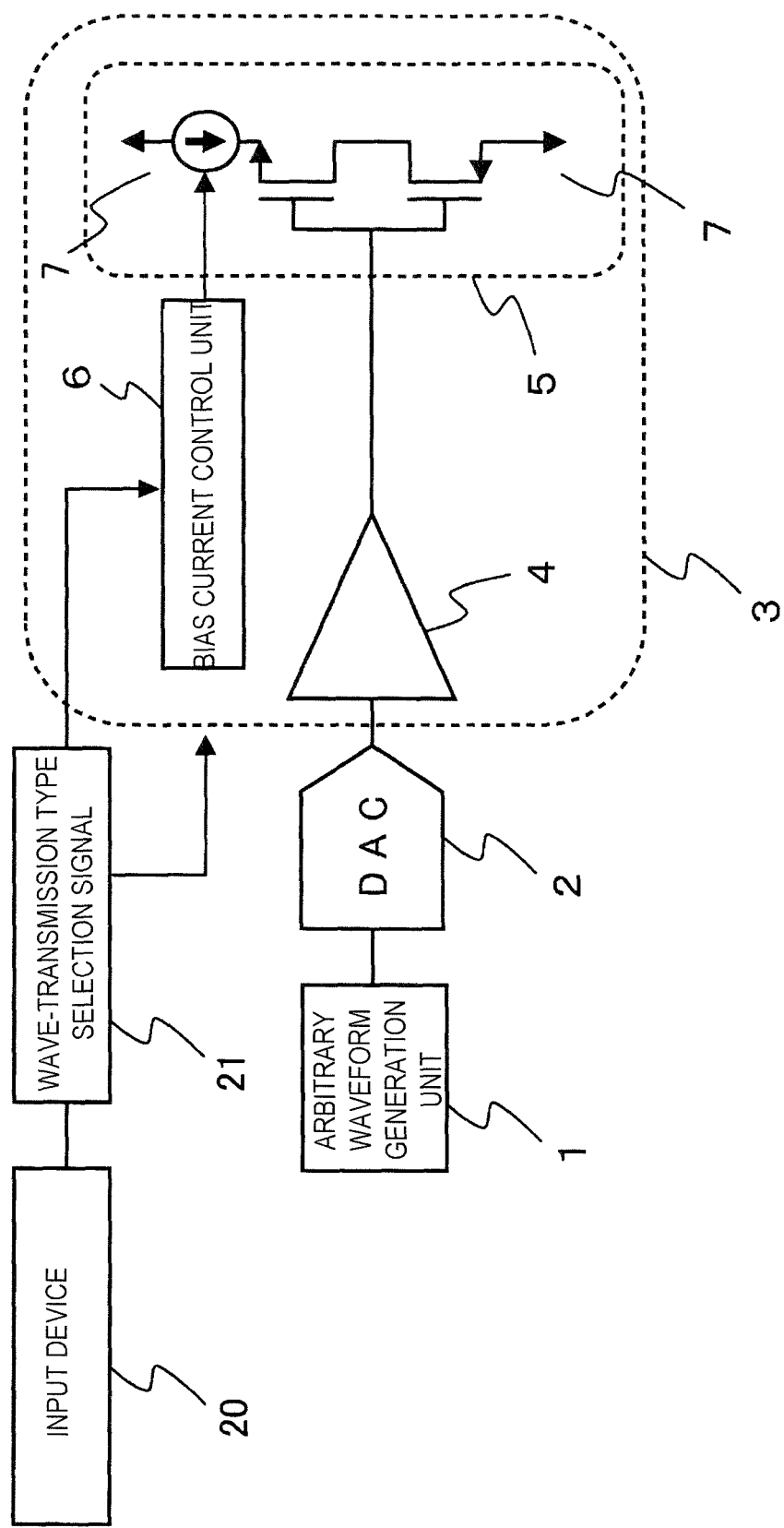
FIG. 1 is a block diagram showing the construction of a transmission circuit in an ultrasonic diagnostic apparatus according to a first embodiment.

First, a transmission circuit of an ultrasonic transducer driving circuit of an ultrasonic diagnostic apparatus is constructed as shown in FIG. 1.

In FIG. 1, the transmission circuit is constructed by an arbitrary waveform generation unit 1 for generating, with a digital signal, any transmission waveform which is necessary to obtain high spatial resolution and is properly weighted and amplitude-controlled in a time-axis direction and an aperture direction for forming a transmission beam, a DA converter (DAC) 2 for converting the transmission waveform to an analog signal, and a wave-transmission amplifier 3 for amplifying this signal until proper amplitude to generate an ultrasonic signal whose size is enough to form a diagnostic image from the transducer described above. 20 represents an input device, and 21 represents a wave-transmission type selection signal output from the input device 20.

The wave-transmission amplifier 3 is more specifically constructed by a signal amplifier 4, and a current amplifier 5 for generating current enough to drive the transducer. In the case of some circuit constructions, the signal amplifier 4 and the current amplifier 5 may be implemented by the same circuit construction. In order to make the description easy, the signal amplifier 4 and the current amplifier 5 are discriminated from each other because they are functionally different from each other, however, actually, they are not limited to this style.

It is now assumed that the current amplifier 5 is formed by FET as a general current amplifying element. Furthermore, it is also assumed that a transmission signal to be transmitted has both positive and negative poles. Therefore, the current amplifier 5 is simply constructed by Pch and Nch, and the Pch and the Nch are connected to each other in a totem-pole (push-pull) style so that current from a power supply 7 flows through D(drain), S(source) portions.

Figure 2:
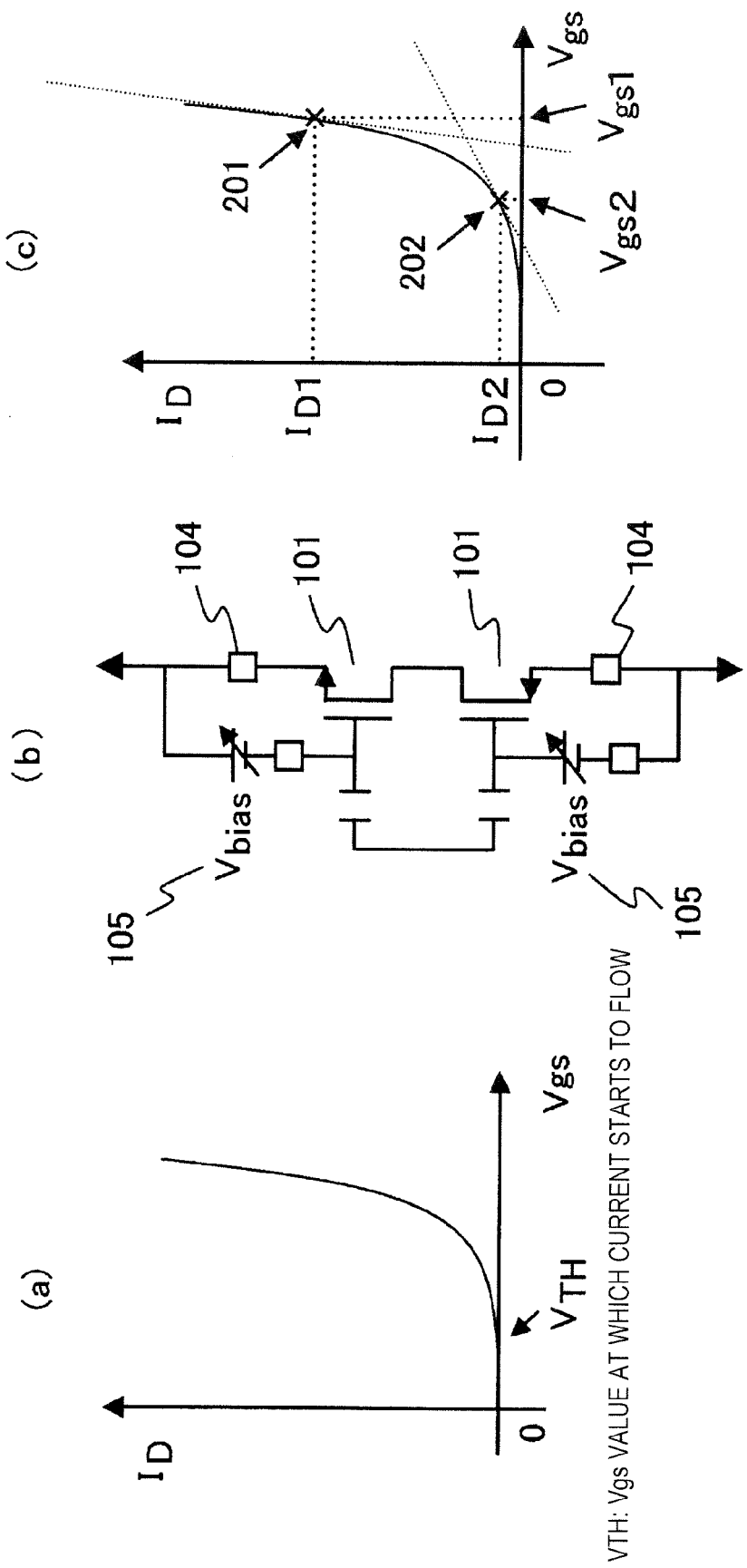
FIG. 2 is a diagram showing the operation of the transmission circuit according to the first embodiment.

In general, FET is known as a switching element, and the characteristic thereof has an exponential function relationship between an input voltage and output current as shown in (a) of FIG. 2. A voltage $V_{GS}$ between G(gate) and S(source) of FET which corresponds to an input voltage in this circuit construction is set on the abscissa axis, and a current amount ($I_D$) corresponding to the voltage $V_{GS}$ is set on the ordinate axis. Furthermore, $V_{TH}$ in (a) of FIG. 2 represents a threshold voltage of FET, and it represents an action point. At values smaller than this voltage, no current basically flows.

As described above, when FET is treated as the current amplifying element, it is necessary to pay attention to the relationship between the operating point and the threshold voltage $V_{TH}$. That is, in order to make an input amplitude and an output amplitude have a fixed amplification degree relationship, a non-responsible band must not be formed with respect to even a small signal input.

In order to obtain an output signal with respect to even an input voltage which is not more than this $V_{TH}$, the minimum operating point of this circuit is required to be set to $V_{TH}$ or more, and in order to satisfy this requirement, it is necessary to apply a voltage of $V_{TH}$ or more to FET at all times. As a result, FET can respond to any small signal, however, even when no signal is input, current steadily flows through FET in some degree. This current will be referred to as bias current.

On the other hand, when the operating point is set to be less than $V_{TH}$, when an input signal is small, this circuit does not operate, and a value of the lowest input signal at which output amplitude is obtained is equal to a predetermined value or more, so that an input signal control width of the output signal is reduced.

Figure 3:
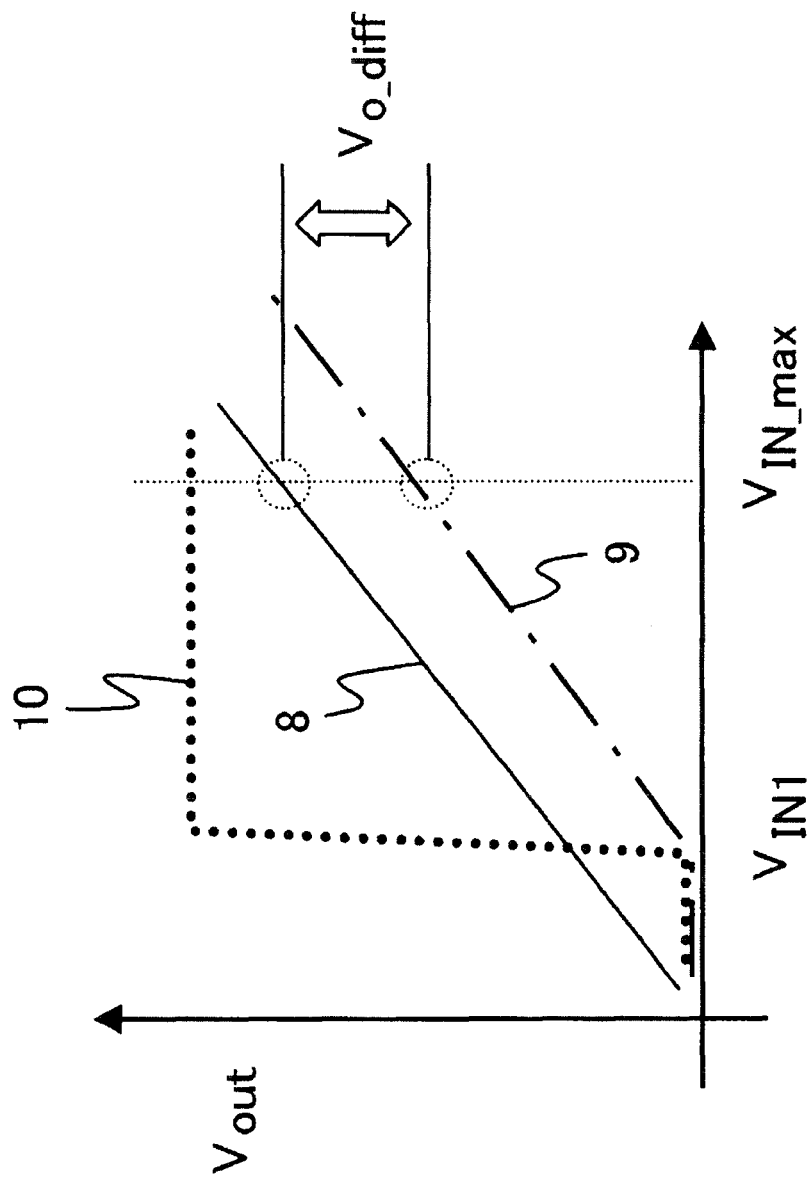
FIG. 3 is a diagram showing the operation of the transmission circuit according to the first embodiment.

FIG. 3 shows an input/output characteristic of the wave-transmission amplifier 3 described above. In FIG. 3, the abscissa axis represents an amplitude value of the input signal, and the ordinate axis represents an output signal amplitude value of the wave-transmission amplifier 3 of FIG. 1. When the operating point is set to $v_{TH}$ or more to provide a linear amplification construction, a linear relationship can be obtained with respect to an amplification degree of the input signal and the output signal, that is, any waveform can be selected for a transmission signal. That is, this provides the construction having the highest effect (highest spatial resolution operation mode) in enhancement of the spatial resolution using waveform weighting although power consumption is increased. This corresponds to a case represented by a solid line 8 of FIG. 3.

When the operating point is set to $V_{TH}$ or less, no output signal is obtained with respect to an input signal smaller than the above value. On the other hand, a linear relationship can be set between the input amplitude and the output amplitude with respect to an input signal of $V_{TH}$ or more. Therefore, transmission of any waveform can be implemented in this range.

In this case, the power consumption is reduced because the operating point is lower than described above. However, a range of the output signal amplitude in an equal input signal amplitude range is narrowed. Therefore, a waveform weighting shape contributing to the enhancement of the spatial resolution is limited, and thus the effect is restricted. This corresponds to a case indicated by a one-dotted chain line 9 in FIG. 3. In FIG. 3, the difference in control range of the output signal amplitude between both the cases is represented by Vo_diff.

With respect to an input/output characteristic in a case of a construction which is generally called as a switching circuit described later, when the input amplitude exceeds some value, the output amplitude thereof is equal to a fixed value determined by a using power supply.

In this case, there is no stationary current consumption, and thus a construction having the lowest power consumption (lowest power consumption mode) can be implemented. However, in a case of a single power supply in which a transmission circuit using power supply has no ch-dependence, it has no waveform weighting function and thus it cannot be expected that the spatial resolution is enhanced. This corresponds to a case indicated by a dashed line 10 in FIG. 3.

The selection between the high spatial resolution operation mode and the low power consumption mode described above can be implemented by using a circuit construction of (b) of FIG. 2, for example. It is now assumed that the amplifier at the last stage of the wave-transmission circuit is constructed as the totem-pole type of FET 101. A bias potential between the gate and the source of FET 101 is represented by Vbias 105. In (b) of FIG. 2, 101 represents a module for impedance insertion, and a block to which Vbias 105 is connected in series likewise represents an impedance element such as a resistor or the like. Vbias 105 is a circuit construction having a variable power supply function, and Vbias 105 and current flowing through FET 101 has the relationship as shown in (c) of FIG. 2. As Vgs corresponding to Vbias increases, a current value increases exponentially.

Taking an example of (c) of FIG. 2, it is now assumed that a potential of Vgs1 is applied as Vbias 105. A current flowing through FET 101 is represented by ID1, and a point 201 acts as a reference point for an AC amplifying action of FET 101. In a region of this point or more, the relationship between the voltage and the current is substantially proportional, and thus this region becomes an area where a linear amplification action is expectable. A case where FET 101 is operated in this region corresponds to the high spatial resolution operation mode in which the power consumption is large, however, the highest priority is given to the resolution.

Furthermore, it is now assumed that a potential of Vgs2 is applied as Vbias 105, a current flowing through FET 101 is represented by ID2, and a point 202 acts as a reference point for the AC amplifying action of FET 101. In a region of this point 202 or more, the relationship between the voltage and the current greatly varies in accordance with the operating point. That is, it is indicated that a linearity of an amplifying action is worse as compared with a case where the point 202 is set as the operating point. However, with respect to the current value flowing steadily, ID2<ID1, and thus the power consumption can be suppressed to a low value. When FET is operated in this region, FET is operated (normal mode) under a state that the resolution and the power consumption are balanced with each other.

Furthermore, when the operating point is set to an original point, that is, when 0V is applied as Vbias, the current value flowing through steadily is equal to zero. However, FET is not turned on unless the input signal thereto is equal to a fixed value (threshold value) or more. A non-response period is long and the linearity as the amplifier is greatly lost, however, the power consumption can be suppressed to the lowest value.

The foregoing description has been made on the basis of the relationship between the power consumption and the linear amplification with limiting the operating point of FET to three points, however, actually, the present invention is not limited to the foregoing description.

Embodiment 1

Figure 4:
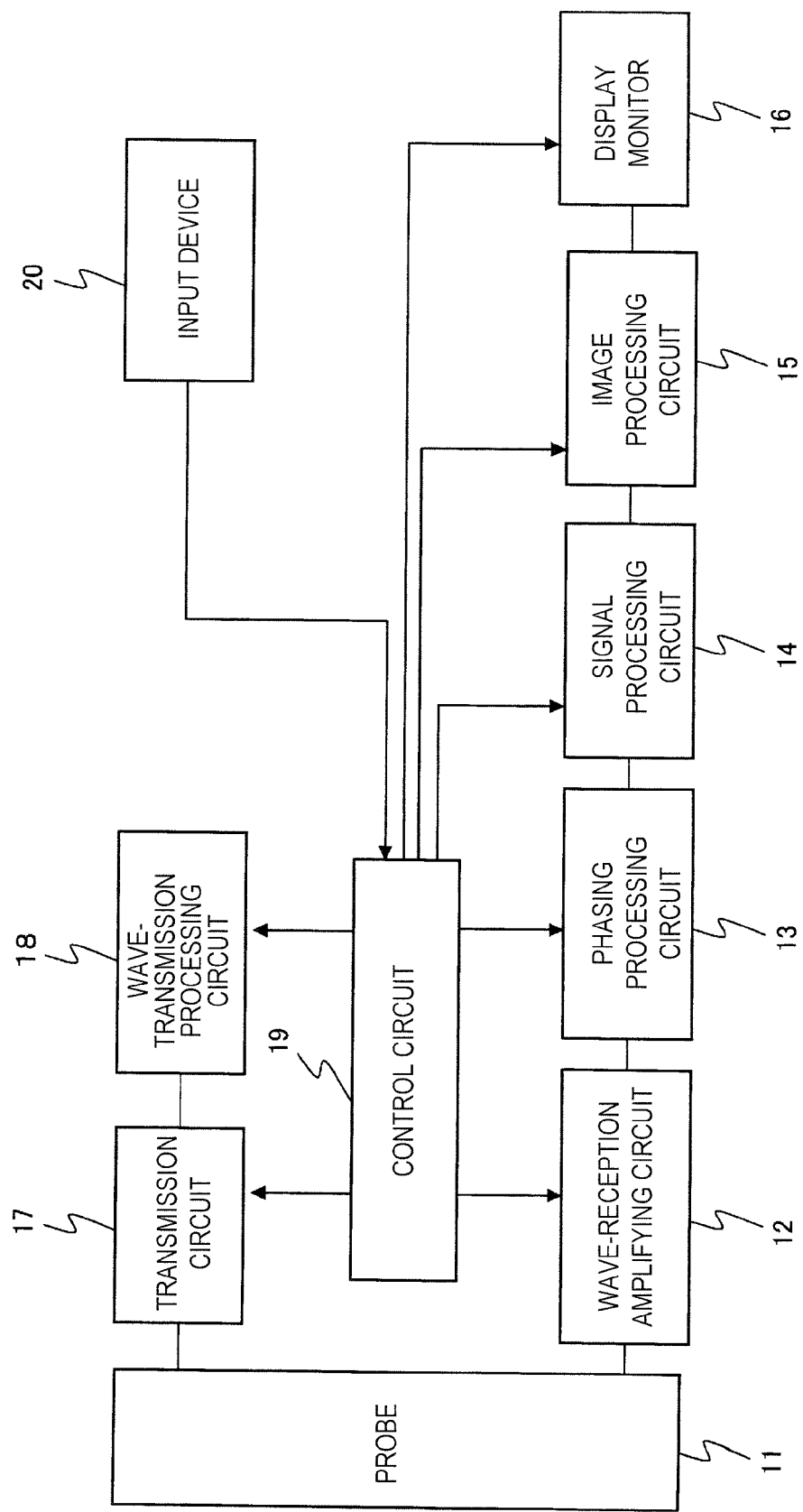
FIG. 4 is a diagram showing the construction of the ultrasonic diagnostic apparatus according to the first embodiment.

FIG. 4 shows an example of the overall construction of an ultrasonic diagnostic apparatus according to a first embodiment. The construction of the device has an ultrasonic probe 11, a wave-transmission processing circuit 18 and a transmission circuit 17 which constitute a transmitter, a wave-reception amplifying circuit 12 and a phasing processing circuit 13 which constitute a receiver, a signal processing circuit 14 and an image processing circuit 15 which constitutes a signal processor, and a display monitor 16 constituting a display unit. As not shown, many transducers are formed in the probe 11 so as to be arranged, and used in close contact with a surface of an object. Each transducer generally has a function of converting a wave-transmission signal of a generally input pulse wave or continuous wave to an ultrasonic wave and emitting the ultrasonic wave to the object, and a function of receiving an ultrasonic wave reflected from the inside of the object and converting the ultrasonic wave to a wave-reception signal of an electric signal and outputting the wave-reception signal.

In each construction circuit, timing control, etc. of each site are performed by a control circuit 19 as a control unit. Furthermore, the control circuit 19 is connected to the input device 20. A user of the device inputs the priority as to suppression of power consumption or enhancement of the spatial resolution through a function described later by inputting the wave-transmission type selecting signal described above through the input device 20.

Figure 5:
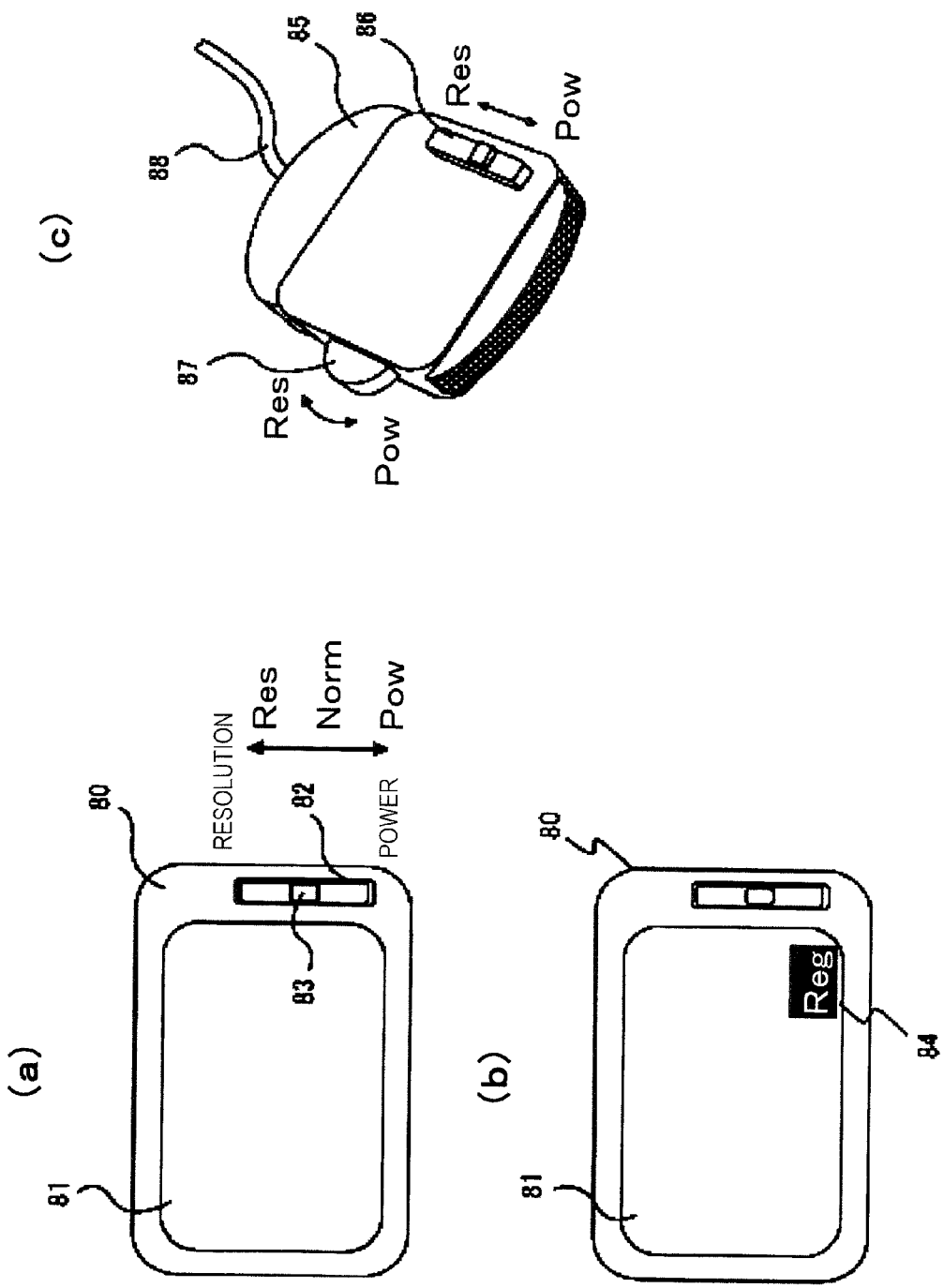
FIG. 5 is a diagram showing a specific construction of an input device 20 of the ultrasonic diagnostic apparatus according to each embodiment.

FIG. 5 is a diagram showing the construction of a specific embodiment of the input device 20 as an input device unit. FIG. 5(a), (b) show the construction when the input device unit is provided on the display monitor 16 of FIG. 4, and FIG. 5(c) shows the construction when the input device unit is provided on the ultrasonic probe 11 of FIG. 4.

An input device unit 82 is provided on a display monitor 80 of FIG. 5(a), and an selecting and switching operation among a high spatial resolution operation mode (Res), a normal mode (Norm) and a low power consumption mode (Pow) is performed by using a slider 83. As shown in FIG. 5(b), a selected mode is displayed as indicted by 84 on a screen 81. FIG. 5(c) shows a case where a switch 86 or 87 is disposed on a part of an ultrasonic probe 85 (in this case, a side surface). The same control as the input device unit 82 can be performed by using the switch 86, 87. It is needless to say that the user manually operates the switch 86, 87 to perform the selecting and switching operation among the high spatial resolution operation mode (Res), the normal mode (Norm) and the low power consumption mode (Pow). 88 represents an input/output cable of the probe 85.

Figure 6:
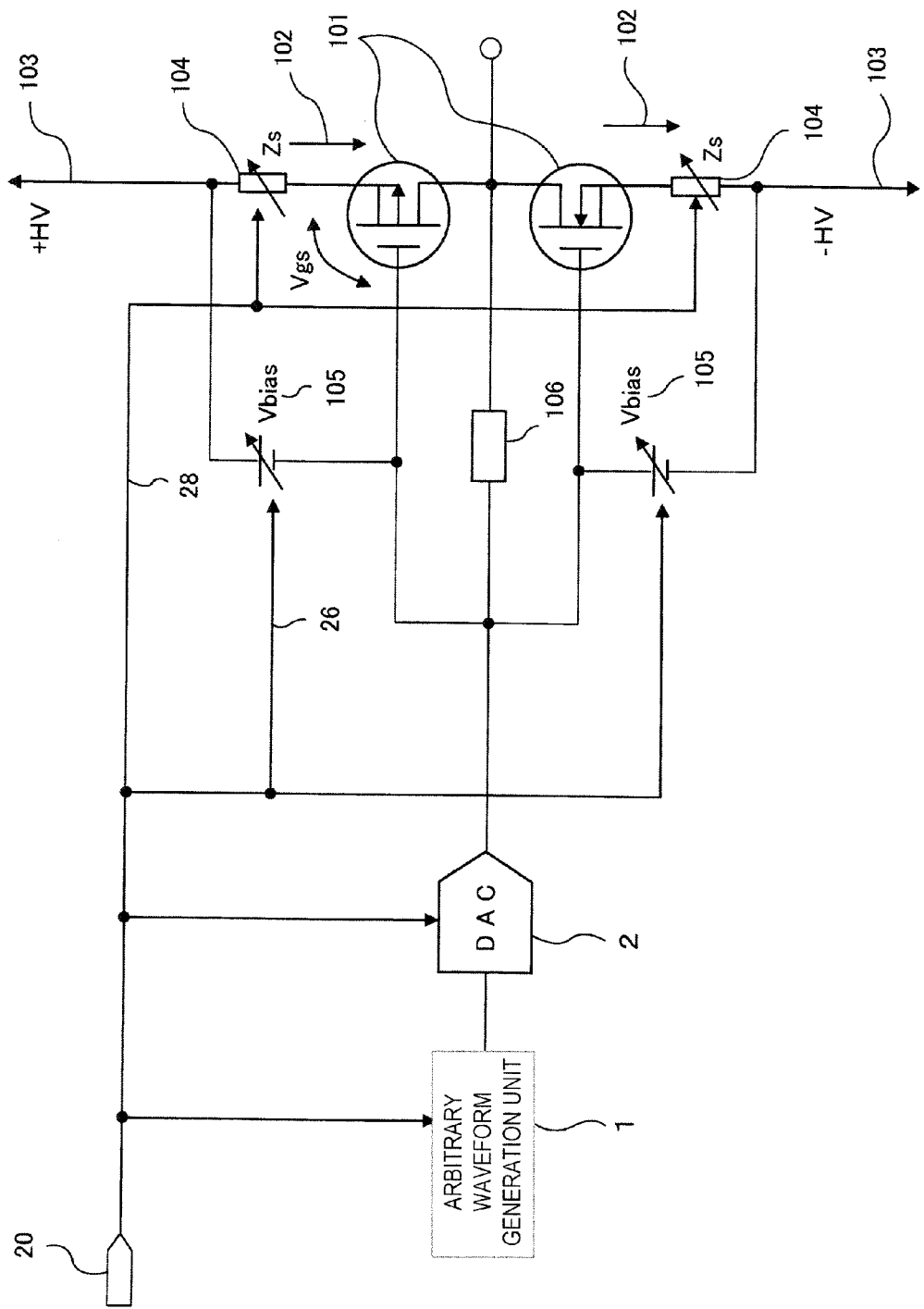
FIG. 6 is a block diagram showing a specific construction of the transmission circuit in the ultrasonic diagnostic apparatus according to the first embodiment.

FIG. 6 shows a specific construction of the transmission circuit 17 according to this embodiment. As in the case of FIG. 2(b), a push-pull circuit based on FET 101 is adopted as the current amplifier 5 for driving the transducer described above, for example. As described above, it is necessary to make bias current 102 flow through this push-pull circuit in the linear amplification transmission circuit in which a fixed amplification degree is kept for the input signal and the output signal at all times.

The bias of FET 101 is configured so as to have a potential difference between the gate of FET 101 and a power supply 103, and thus bias current flows from the power supply 103 to the source/drain of FET 101. A module 104 having an impedance Zs for adjusting a DC current amount, which is represented by a resistor, is disposed to adjust the amount of bias current. Accordingly, when the bias potential 105 is represented by Vbias and the potential between the gate and source of FET 101 is represented by Vgs, a bias current Id is represented by the expression (1).

$$Id = (Vbias - Vgs)/Zs \qquad (1)$$

Accordingly, the circuit of FIG. 6 can be operated as a linear amplifying circuit. It is preferable that a feedback mechanism 106 such as a feedback resistor or the like is provided between the input and the output in the linear amplifying operation circuit having higher precision. However, the feedback mechanism 106 is not described in detail because attention is particularly paid to the relationship between the bias current and the waveform.

In this case, a stationary power consumption Wall of the transmission circuit unit is provided according to the expression (2). Here, N represents the number of transmission circuits per device.

$$Wall = \{|(+HV)| \times Id + |(-HV)| \times Id\} \times N \qquad (2)$$

A value indicated by the solid line 8 of FIG. 3 is expected for the input/output characteristic of the transmission circuit under this condition.

In the circuit shown in FIG. 6, Vbias represented by the bias potential 105 or the impedance value represented by the module 104 is adjusted by control signals 26, 28 from the input device 20, whereby the operating point of FET 101 can be changed as described above. Specifically, the magnitude of the bias potential can be changed by giving DC potential and adjusting the value of current flowing through FET on the basis of an instruction from the input device 20, however, the present invention is not limited to this construction.

Accordingly, the input/output characteristic of this circuit can be changed as indicated by the one-dotted chain line 9 in FIG. 3, and this corresponds to a case where the bias current 102 is reduced.

Furthermore, it is considered that the bias potential Vbias is equal to 0V, that is, the power supply 103 and the gate portion of FET 102 are set to the same potential in the DC level by the control signal 21. Actually, an electrical element such as a resistor or the like (not shown) is disposed between the power supply 103 and the gate of FET 102. Furthermore, no bias current flows, and thus Zs is also set to be short-circuited by the control signal.

In this case, the circuit of FIG. 3 has a construction which is so-called as a switching circuit, and it basically outputs a fixed output signal determined by the power supply 103 with respect to an input signal which exceeds a threshold voltage. No bias current flows and thus the power consumption is suppressed to the minimum value. However, the output signal is fixed at all times irrespective of the amplitude of the input signal, and thus an amplitude weighting function required to enhance the spatial resolution is lost.

Furthermore, in this case, the input signal may be a binary signal for which the threshold value is set to $V_{TH}$, and thus the construction of the arbitrary waveform generation unit is changed so that only 0 and VIN which are simple binary signals are output by the control signal 21. Furthermore, DAC 2 may be changed so as to have a simple output construction for outputting only the most significant bit (MSB), for example.

That is, as described above, by controlling a bias state of the transmission circuit, the variation of the output signal to the input signal is shown in FIG. 3, and not only current consumption can be controlled, but also the output signal value thereof can be controlled. As a result, a controllable range of a transmission-wave amplitude weighting is controlled, and thus the spatial resolution of the ultrasonic diagnostic image can be changed.

As described above, in the first embodiment shown in FIG. 6, only one set of positive and negative transmission power supplies 103 is provided. However, actually, the present invention is not limited to this style. For example, there may be considered a case where the power supply at the negative side (−HV) may be grounded in the switching circuit construction.

Furthermore, this embodiment is also effective to a transmission circuit having a mechanism which can weight the output signal by some control even when the input signal and the output signal do not have any integral-multiple linear amplification relationship.

Embodiment 2

Figure 7:
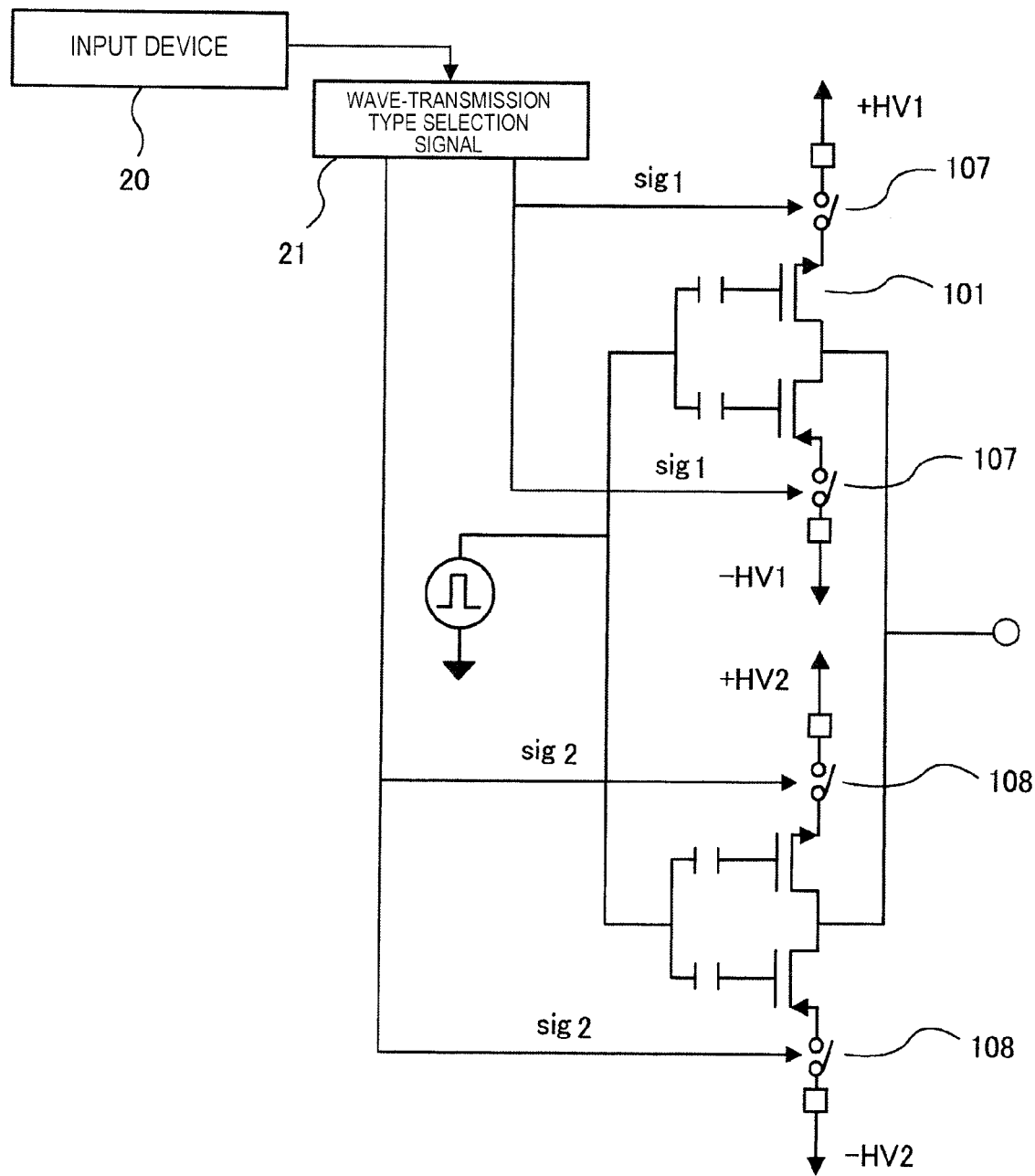
FIG. 7 is a diagram showing a specific construction of a transmission circuit in an ultrasonic diagnostic apparatus according to a second embodiment.

As a second embodiment, a circuit construction using plural power supplies (HV1, HV2) to generate one wave-transmission signal and a waveform of the signal will be described with reference to FIGS. 7 and 8. FIG. 7 shows a circuit construction which can have values of ±2 stages at maximum as a wave-transmission signal amplitude.

Figure 8:
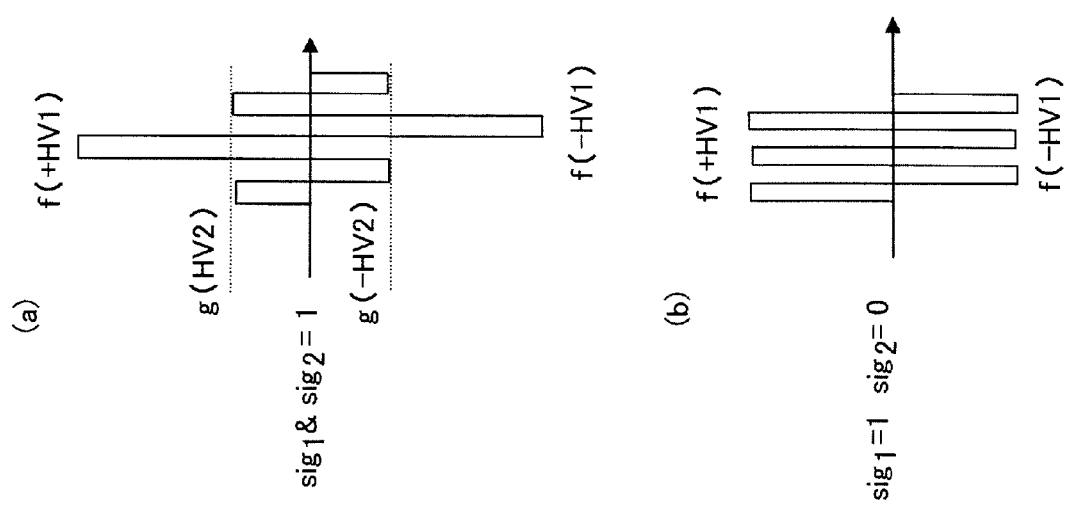
FIG. 8 is a diagram showing an output waveform of the transmission circuit of the ultrasonic diagnostic apparatus shown in FIG. 7.

In FIGS. 7 and 8, two switch circuits are connected in parallel to output one wave-transmission signal. The respective switch circuits are connected to ±HV1, ±HV2 respectively, and output signals thereof are determined by power supply values.

Now, it is assumed that each of switches 107, 108 is provided between each FET 101 and the power supply connected to the FET 101. The switches 107, 108 have a characteristic that they are set to ON when 1 is input to the switches as a signal and set to OFF when 0 is input to the switches.

The switches 107 and 108 operate commonly in a totem-pole (push-pull) type which is independent on each FET 101 or common to an output of FET.

sig1 is input to the switch 107 which determines the operation of FET 101 connected to ±HV1, and sig2 is input to the switch 108 which determines the operation of FET 101 connected to ±HV2.

There is now considered a case where sig1 and sig 2 are set to ON. Such a signal as shown in FIG. 8(a) can be output as an output signal. In this case, it is assumed that a current value l1 mA steadily flows through FET 101 connected to ±HV1, and l2 mA flows through FET 101 connected to ±HV2.

Furthermore, in a case of sig1=1 and sig2=0, no current flows through FET 101 connected to ±HV2, and no output signal exists. Since ±HV1 is set to ON, the output signal becomes a waveform having a single value which is not weighted as shown in FIG. 8(b). Furthermore, the input device 20 and the wave-transmission type selection signal 21 are the same for both the circuits, and thus they are commonly shown.

FIG. 7 shows a case where the circuits using the power supplies 103 of ±HV1 and ±HV2 have a common output. In this case, the output signal is controlled by the value caused by each power supply, and for example it is assumed that first and third waves are controlled by the circuit having ±HV2 as the power supply and a second wave is controlled by the circuit having ±HV1 as the power supply as shown in FIG. 8(a). That is, waveform weighting effect is applied, and the enhancement of the spatial resolution described above is expectable.

It is assumed that current of l1 mA is consumed in the circuit using ±HV1 at all times and current of l2 mA is consumed in the circuit using ±HV2 at all times. In this case, a power W1 represented by the expression (3) is consumed.

$$W1=\{(+HV1)-(-HV1)\}\times l1+\{(+HV2)-(-HV2)\}\times l2 \quad (3)$$

Next, it is assumed that a stationary power consumption of the circuit having ±HV2 as the power supply is set to 0 by the control from the input device 20 as shown in FIG. 8(b), that is, the circuit is not used.

In this case, the output signal is shown in FIG. 8(b), and the circuit having ±HV2 does not contribute to the output signal.

Accordingly, the stationary power consumption is represented by the expression (4), and only ±HV1 contributes. Therefore, the power is lower as compared with the expression (3).

$$W2=\{(+HV1)-(-HV1)\}\times l1 \quad (4)$$

The above-described embodiment shown in FIGS. 7 and 8 has respective two kinds of positive and negative power supply absolute values. However, actually, this embodiment is not limited to this style, and it is needless to say that the substance of this embodiment is not lost even when the embodiment is constructed by a circuit having more power supplies.

The present invention is also particularly effective to an ultrasonic diagnostic apparatus used as a hand carry unit (HCU).

DESCRIPTION OF REFERENCE NUMERALS 1 arbitrary waveform generation unit, 2 DA converter, 3 transmission waveform amplifier, 4 signal amplifier, 5 current amplifier, 7 transmission circuit power supply, 11 probe, 12 wave-reception amplifier, 13 phasing processing circuit, 14 signal processing circuit, 15 image processing circuit, 16, 80 display monitor, 17 transmission circuit, 18 wave-transmission processing circuit, 19 control circuit, 20, 82 input device, 86, 87 switch, 101 FET, 102 bias current, 103 power supply, 104 impedance module, 105 bias potential, 106 feedback mechanism, 107, 108 switch

The invention claimed is:

1. An ultrasonic diagnostic apparatus comprising:
   an ultrasonic probe configured to transmit and receive an ultrasonic wave;
   a transmitter configured to supply a signal to the ultra sonic probe and from an ultrasonic beam;
   a receiver configured to receive a reception signal obtained by transmitting the ultrasonic beam to an object;
   a signal processor configured to form an ultrasonic image based on the reception signal;
   a display unit configured to display the ultrasonic image; and
   a control unit configured to control the transmitter, the receiver, the signal processor and the display unit,
   wherein the control unit comprises a setting unit configured to set an operation mode of the transmitter to a low power consumption operation mode or a high spatial resolution operation mode, and
   wherein the transmitter comprises a FET (Field Effect Transistor), and the low power consumption operation mode and the high spatial resolution operation mode of the transmitter are selected by controlling bias current to a source and a drain of the FET.

2. The ultrasonic diagnostic apparatus according to claim 1, further comprising:
   an input device unit,
   wherein the bias current is controlled based on a wave-transmission type selection signal from the input device unit.

3. The ultrasonic diagnostic apparatus according to claim 1, wherein the transmitter comprises a first FET connected to a first power supply and a second FET connected to a second power supply, and the low power consumption operation mode and the high spatial resolution operation mode of the transmitter are selected by controlling bias current to a source and a drain of the first FET and to a source and a drain of the second FET.

4. The ultrasonic diagnostic apparatus according to claim 3,
   wherein the setting unit is an input device unit, and
   wherein the bias current is controlled based on a wave-transmission type selection signal from the input device unit.

5. The ultrasonic diagnostic apparatus according to claim 4,
   wherein the first FET and the second FET are connected to the first power supply and the second power supply, respectively, through a switch, and
   wherein the switch is controlled to be turned on/off by the wave-transmission signal selection signal.

* * * * *